United States Patent
Mahrouche (10) Patent No.: US 8,298,218 B2
(45) Date of Patent: Oct. 30, 2012

(54) COMPLIANT BALLOON

(75) Inventor: Rachid Mahrouche, Québec (CA)

(73) Assignee: Medtronic Cryocath LP, Toronot, Ontario (CA)

( * ) Notice: Subject to any disclaimer, the term of this patent is extended or adjusted under 35 U.S.C. 154(b) by 549 days.

(21) Appl. No.: 12/511,403

(22) Filed: Jul. 29, 2009

(65) Prior Publication Data

US 2011/0029048 A1   Feb. 3, 2011

(51) Int. Cl.
*A61B 18/12* (2006.01)
(52) U.S. Cl. .......... 606/21; 606/192
(58) Field of Classification Search .......... 606/20–26, 606/192–194; 604/264
See application file for complete search history.

(56) References Cited

U.S. PATENT DOCUMENTS

| | | | |
|---|---|---|---|
| 4,364,392 A | 12/1982 | Strother et al. | |
| 5,277,201 A * | 1/1994 | Stern | 607/98 |
| 6,575,966 B2 * | 6/2003 | Lane et al. | 606/21 |
| 7,641,668 B2 * | 1/2010 | Perry et al. | 606/192 |
| 7,758,572 B2 * | 7/2010 | Weber et al. | 606/23 |
| 2002/0183620 A1 * | 12/2002 | Tearney et al. | 600/473 |
| 2003/0060813 A1 | 3/2003 | Loeb et al. | |
| 2007/0244501 A1 * | 10/2007 | Horn et al. | 606/194 |

FOREIGN PATENT DOCUMENTS

WO   03020334 A2   3/2003

* cited by examiner

*Primary Examiner* — Michael Peffley
(74) *Attorney, Agent, or Firm* — Christopher & Weisberg, P.A.

(57) ABSTRACT

A cryogenic medical device is provided, including a catheter body defining a proximal portion and a distal portion; a expandable treatment element on the distal portion of the catheter body; a plurality of granules disposed within the expandable treatment element; an encapsulation member surrounding the plurality of granules, the encapsulating member having a plurality of selectable geometric configurations; and an actuator element coupled to the encapsulation member for the selective adjustment thereof. A method for thermally treating a selected region of tissue is also provided.

18 Claims, 8 Drawing Sheets

COMPLIANT BALLOON

CROSS-REFERENCE TO RELATED APPLICATION

N/A

STATEMENT REGARDING FEDERALLY SPONSORED RESEARCH OR DEVELOPMENT

N/A

FIELD OF THE INVENTION

The present invention relates to a medical method and system having a selectively configurable treatment element, and a method and system for modifying and controlling tensioning and/or varying the shape of a treatment element.

BACKGROUND OF THE INVENTION

Numerous procedures involving catheters and other minimally invasive devices may be performed to provide a wide variety of treatments, such as ablation, angioplasty, dilation or the like. For example, an ablation procedure may involve creating a series of inter-connecting lesions in order to electrically isolate tissue believed to be the source of an arrhythmia. During the course of such a procedure, a physician may employ several different catheters having variations in the geometry and/or dimensions of the ablative element in order to produce the desired ablation pattern. Multiple devices having varying dimensions and/or shapes may also be employed to account for variations in anatomical dimensions from patient to patient. Each catheter may have a unique geometry for creating a specific lesion pattern or size, with the multiple catheters being sequentially removed and replaced to create the desired multiple lesions. Exchanging these various catheters during a procedure can cause inaccuracies or movement in the placement and location of the distal tip with respect to the tissue to be ablated, and may further add to the time required to perform the desired treatment. These potential inaccuracies and extended duration of the particular procedure increase the risk to the patient undergoing treatment.

In addition, when a balloon is employed, it often must be manufactured or constructed to have a particular shape or dimension for a specific application, and as such, any given catheter with a balloon may be limited to use in situations where the fixed dimensions of the balloon are appropriate. For example, a balloon may have a fixed radius in an inflated state, making it only suitable for a procedure requiring such a dimension or where a particular vasculature may accommodate that radius. As such, multiple catheters having varying fixed dimensions may be needed to successfully perform a desired treatment or to account for variations between patients.

In light of the above, it is desirable to provide a medical device providing various controllable shapes or dimensions, thereby reducing or eliminating the need for additional medical devices having varied, but limited geometric orientations, and thus, limited ability to provide multiple ablative patterns or sizes.

SUMMARY OF THE INVENTION

The present invention advantageously provides a medical device providing various controllable shapes or dimensions, thereby reducing or eliminating the need for additional medical devices having varied, but limited geometric orientations, and thus, limited ability to provide multiple ablative patterns or sizes. In particular, a medical device is provided having a thermal treatment element; and a plurality of granules disposed within the thermal treatment element, the plurality of granules being selectively transitionable from a first geometric configuration to a second geometric configuration; and an encapsulation member at least partially surrounding the plurality of granules. The encapsulation member may be controllably adjustable to cause the plurality of granules to transition from the first geometric configuration to the second geometric configuration, and the device may include an actuator element coupled to the encapsulation member for selective adjustment thereof. A tensioning element may bias the plurality of granules towards the first geometric configuration.

A cryogenic medical device is also provided, having a catheter body defining a proximal portion and a distal portion; an expandable treatment element on the distal portion of the catheter body; a plurality of granules disposed within the expandable treatment element; an encapsulation member surrounding the plurality of granules, the encapsulating member having a plurality of selectable geometric configurations; and an actuator element coupled to the encapsulation member for the selective adjustment thereof. The device may further include a tensioning element coupled to the encapsulation member, where the tensioning element biases the encapsulation member towards a pre-determined geometric configuration. A handle element may be coupled to the proximal portion of the catheter body, and the tensioning element and the actuator element may be coupled to the handle element. The actuator element may be releasably securable in a plurality of discrete positions on the handle element, and the device may include a size detection element (such as a resistance element, a capacitance element, or an impedance element) coupled to the treatment element.

A method for thermally affecting a tissue region (such as cardiac tissue) is also provided, including positioning a treatment element of a medical device proximate a tissue region, the treatment element containing a plurality of granules in a first geometric configuration; controllably transitioning the plurality of granules from the first geometric configuration to a second geometric configuration; and delivering a cryogenic coolant into the treatment element, thereby thermally affecting the tissue region. The medical device may include an encapsulation member surrounding the plurality of granules, and controllably transitioning the plurality of granules from the first geometric configuration to a second geometric configuration includes manipulating an actuator element coupled to the encapsulation member. The method may include terminating the cryogenic coolant delivery, and controllably transitioning the plurality of granules from the second geometric configuration to the first geometric configuration or controllably transitioning the plurality of granules from the second geometric configuration to a third geometric configuration.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
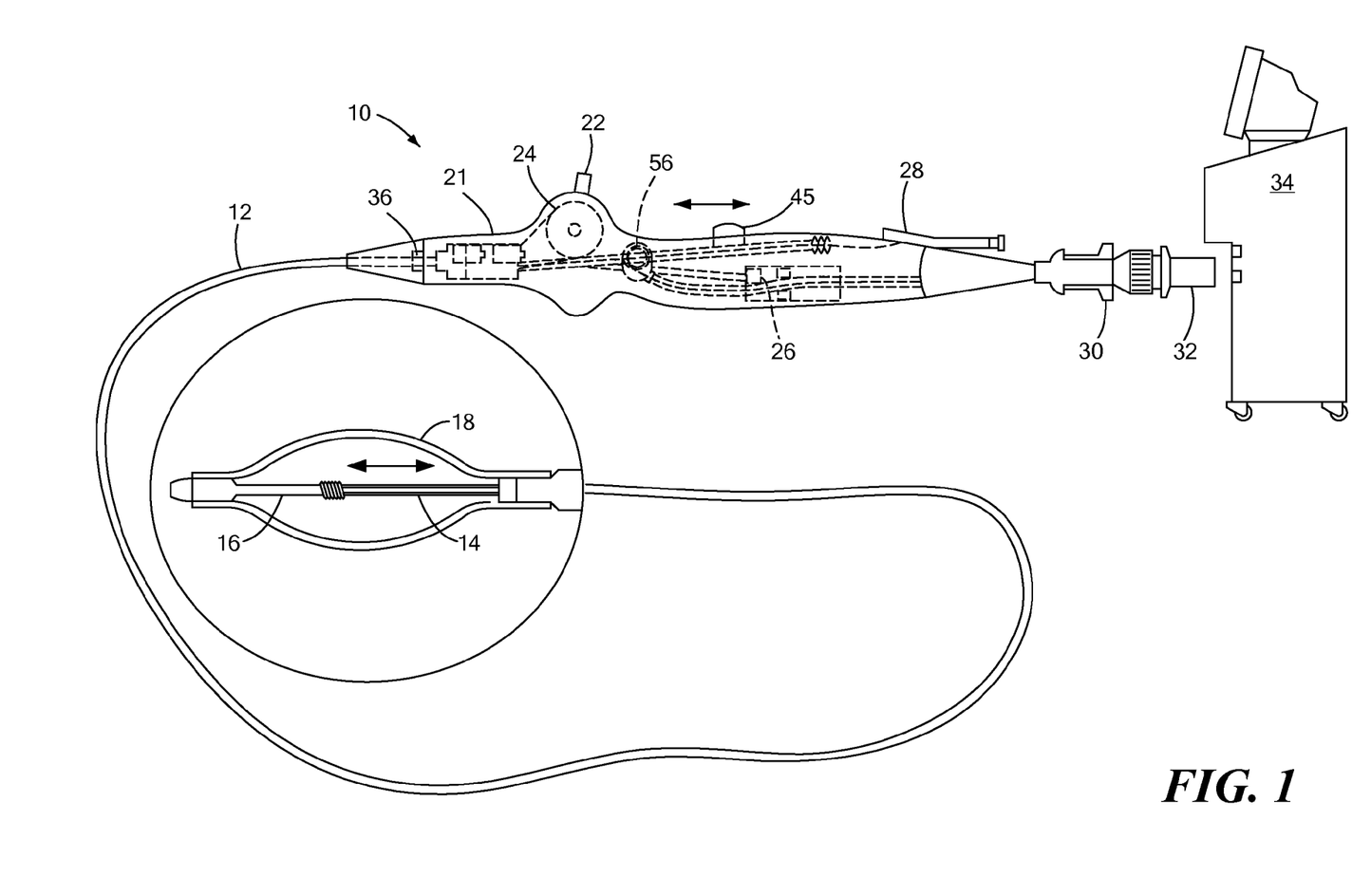
FIG. 1 illustrates an embodiment of a medical device in accordance with the present invention.
Figure 2:
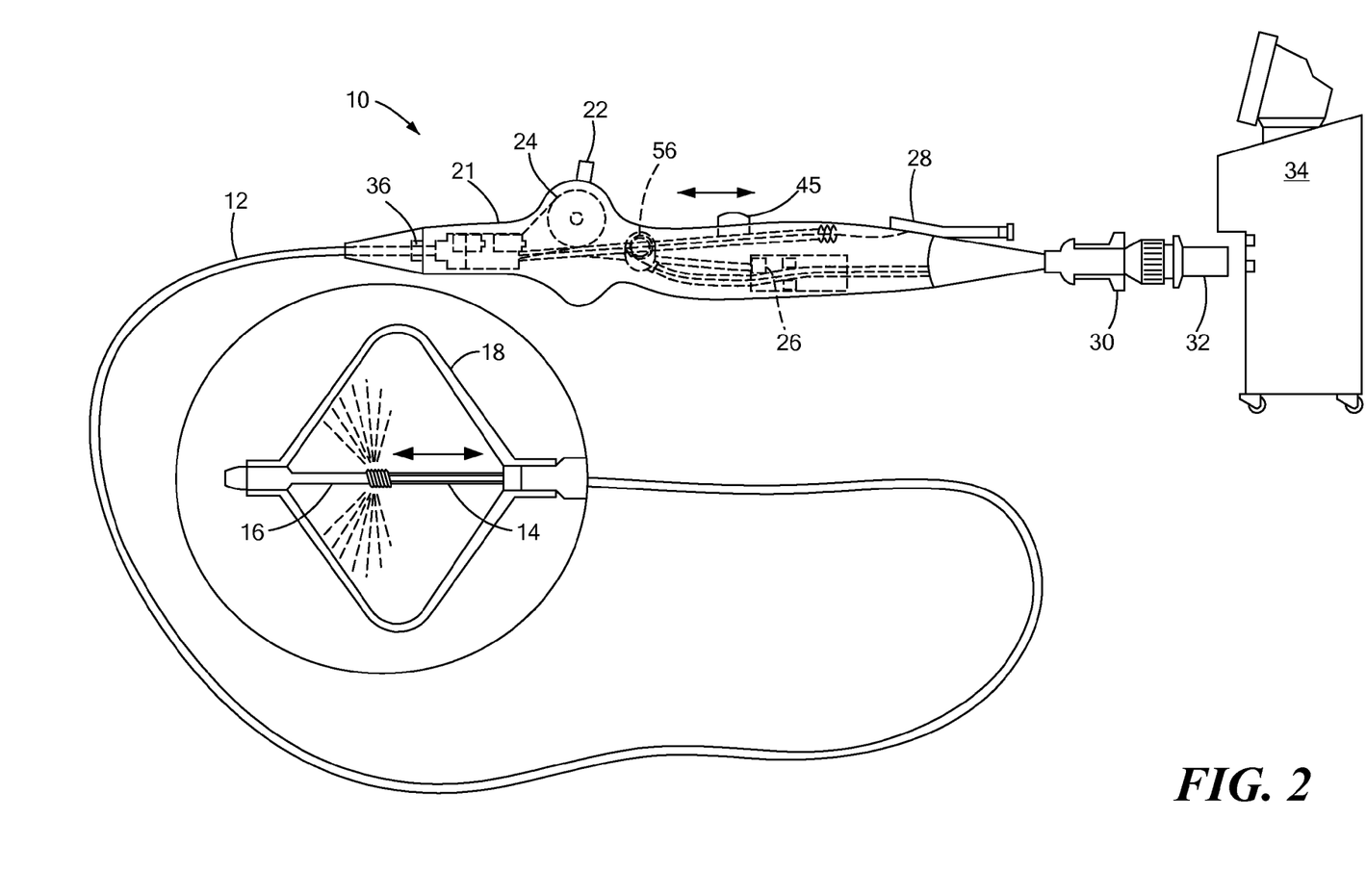
FIG. 2 is an additional illustration of the medical device of FIG. 1.
Figure 3:
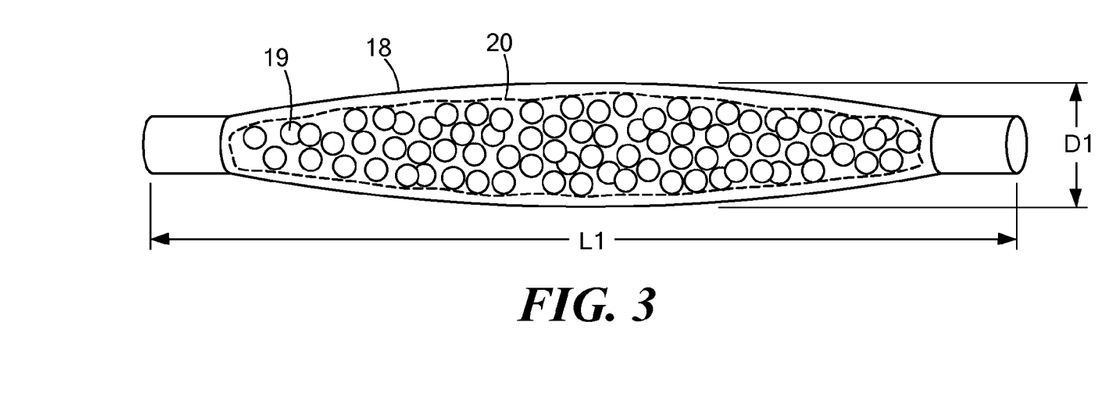
FIG. 3 depicts an embodiment of a treatment element in a first geometric configuration in accordance with the present invention.
Figure 4:
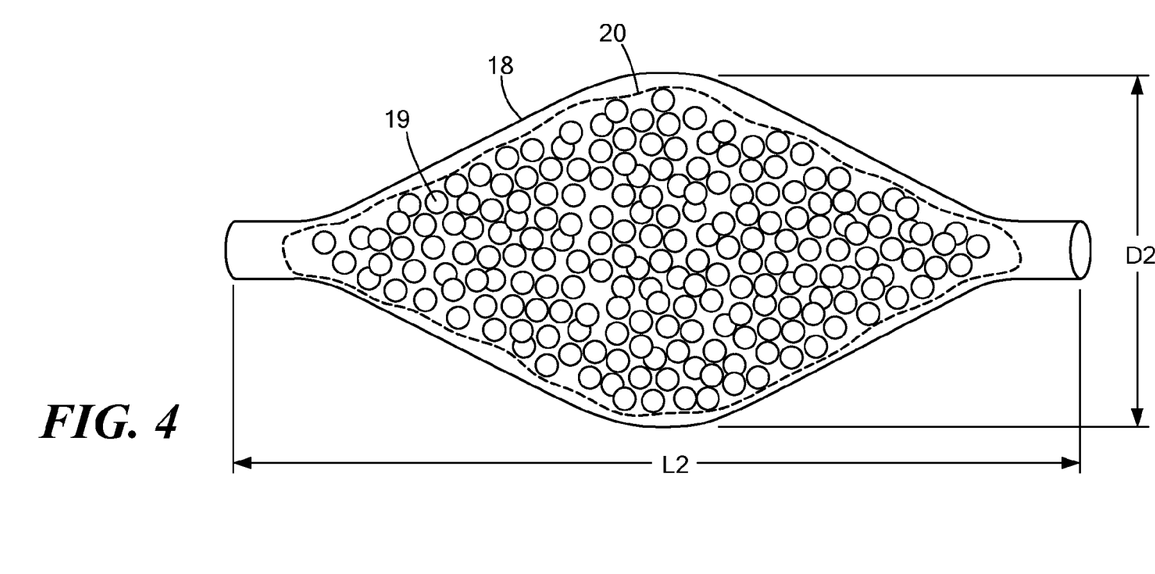
FIG. 4 shows an embodiment of a treatment element in a second geometric configuration in accordance with the present invention.
Figure 5:
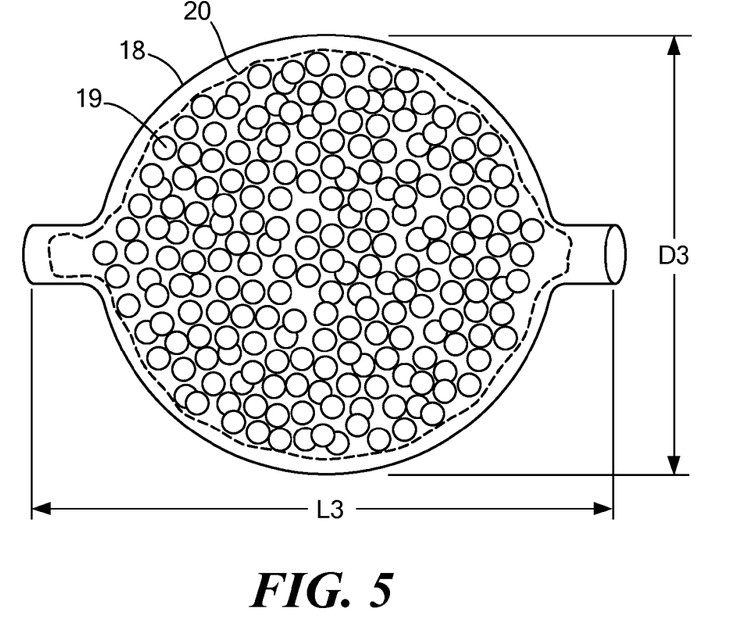
FIG. 5 illustrates an embodiment of a treatment element in a third geometric configuration in accordance with the present invention.
Figure 6:
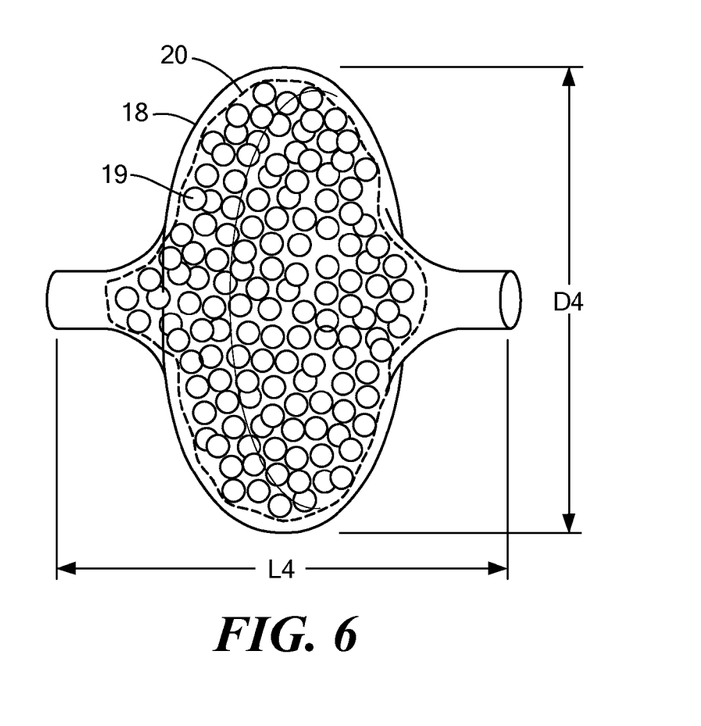
FIG. 6 also illustrates an embodiment of a treatment element in another geometric configuration in accordance with the present invention.

Now referring to FIGS. 1 and 2, an embodiment of the present invention provides a medical device, generally designated as 10. The medical device 10 may include an elongate body 12, such as a catheter. The elongate body 12 may define a proximal portion and a distal portion, and may further include one or more lumens disposed within the elongate body 12 to provide mechanical, electrical, and/or fluid communication between the proximal portion of the elongate body 12 and the distal portion of the elongate body 12. For example, the elongate body 12 may include an injection lumen 14 and an exhaust lumen defining a fluid flow path therethrough. In addition, the elongate body 12 may include a guidewire lumen 16 movably disposed within and/or extending along at least a portion of the length of the elongate body 12 for over-the-wire applications. The guidewire lumen 16 may define a proximal end and a distal end, and the guidewire lumen 16 may be movably disposed within the elongate body 12 such that the distal end of the guidewire lumen 16 extends beyond and out of the distal portion of the elongate body 12.

The medical device 10 of the present invention may further include a treatment element 18 at least partially disposed on the elongate catheter body to provide thermal treatment to a selected tissue area. The treatment element 18 may include one or more balloons or other expandable structure defining a proximal end coupled to the distal portion of the elongate body 12 of the catheter, while further defining a distal end coupled to the distal end of the guidewire lumen 16. As such, due to the movable nature of the guidewire lumen 16 about the elongate body 12, any axial and/or longitudinal movement of the guidewire lumen 16 may act to tension or loosen the treatment element 18, i.e., extend or retract the treatment element 18 from a lengthened state to a shortened state during deflation or inflation, respectively. In addition, the treatment element 18 may have any of a myriad of shapes, and may further include one or more material layers providing for safety, puncture resistance, radiopacity, or the like. The treatment element 18 may be in communication with the fluid injection and exhaust lumens of the medical device 10 as described above. The lumens can define a fluid flow path to provide a treatment fluid, such as a cryogenic fluid or the like, to the interior of the treatment element 18. In addition, a sheath (not shown) may be provided which is slidably positionable about at least a portion of the elongate body 12 of the medical device 10 and/or the treatment element 18.

The medical device 10 may further include a plurality of granules 19 disposed within at least a portion of the treatment element that can be selectively manipulated into multiple geometric configurations, such as those shown in FIGS. 3-6. The selective manipulation of the plurality of granules 19 provides the availability of several different, discrete geometric profiles or shapes the treatment element 18 can attain to provide resulting treatment to tissue regions of varying dimension. The granules 19 may be constructed from ceramics, metals, polymers, or composites thereof to provide desired thermal characteristics, biocompatibility, and material strength. Further, the granules 19 may be constructed from a thermally conductive material capable of absorbing heat (such as aluminum, for example) during a particular treatment regimen, such as cryoablation. The granules 19 may further include a substantially rounded or spherical shape, having a diameter in the range of approximately 1 mm to approximately 2 mm. Of course, variations in size and shape may be implemented for specific applications.

In addition to providing selective shaping or dimensional capability for the treatment element 18, the granules 19 may further provide a degree of structural rigidity or support to reduce or otherwise eliminate the need for the introduction of an inflation medium, such as a cryogenic coolant, into the treatment element 18 for placement and configuration inside the patient (discussed below).

The medical device 10 of the present invention may further include an encapsulation member 20 at least partially disposed within the treatment element 18 and surrounding the plurality of granules 19. The encapsulation member 20 may be configurable into a plurality of geometric configurations, provide for the selective manipulation of the plurality of granules 19, and prevent the aspiration or migration of granules along the length of the elongate body 12. The encapsulation member 20 may define a mesh or wire structure, and may be constructed from a combination of elastic materials, non-elastic materials, and/or shape-memory materials, such as a nickel-titanium alloy or the like, for example. A particular geometric configuration of the encapsulation member 20 (and thus the granules 19 and treatment element 18) may be achieved through the application of mechanical force, thermal energy, magnetic energy, and/or electrical energy. For example, the encapsulation member 20 may be predisposed and/or biased towards a first geometric configuration, which may include a substantially elongated, cylindrical shape. Upon the application of a particular mechanical, thermal, and/or electrical force, the encapsulation member 20 may be selectively transitioned from the first geometric configuration to a second geometric configuration, having a substantially spherical shape, for example. As discussed, the transition from a first particular configuration to a second particular configuration of the encapsulation member 20 may be achieved by the application of mechanical, thermal, or electrical forces.

The medical device 10 may include a handle element 21 coupled to the proximal portion of the elongate body 12, where the handle may include an element such as a lever or knob 22 for manipulating the catheter body and/or additional components of the medical device 10. For example, a pull wire with a proximal end and a distal end may have its distal end anchored to the elongate body 12 at or near the distal end. The proximal end of the pull wire may be anchored to an element such as a cam 24 in communication with and responsive to the lever. The handle 21 can further include circuitry for identification and/or use in controlling of the medical device 10 or another component of the system. For example, the handle may include one or more pressure sensors 26 to monitor the fluid pressure within the medical device 10. Additionally, the handle may be provided with a fitting 28 for receiving a guidewire that may be passed into the guidewire lumen 16, which may be partially disposed within the elongate body 12.

The handle 21 may also include connectors that are matable directly to a fluid supply/exhaust and control unit or indirectly by way of one or more umbilicals for providing fluid communication with the second elongate body 12. For example, the handle may be provided with a first connector 30 that is matable with a co-axial fluid umbilical (not shown) and a second connector 32 that is matable with an electrical umbilical (not shown) that can further include an accessory box (not shown). In an exemplary system, a fluid supply and exhaust, as well as various control mechanisms for the system may be housed in a single console or control unit 34. In addition to providing an exhaust function for the catheter fluid supply, the console 34 may also recover and/or re-circulate fluid delivered to the handle 20 and the elongate body 12 of the medical device 10. A vacuum pump in the console may create a low-pressure environment in one or more conduits within the catheter body so that fluid is drawn into the conduit (s), away from the treatment element 18, and towards the proximal end of the catheter.

Figure 7:
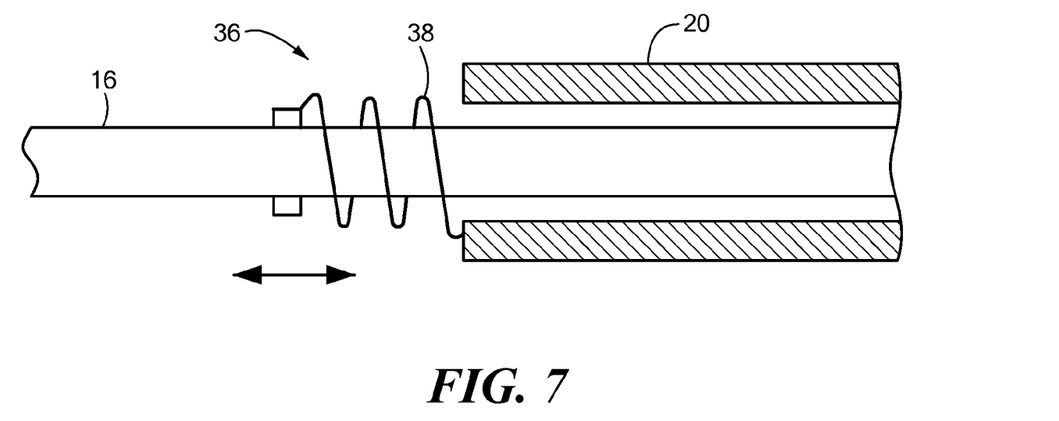
FIG. 7 illustrates an embodiment of a tensioning element in accordance with the present invention.

Now referring to FIGS. 7-10, the medical device 10 of the present invention may include a tensioning element 36 coupled to a portion of the guidewire lumen 16 and/or the handle element 21. The tensioning element 36 may provide a biasing force that predisposes or urges a portion of the guidewire lumen 16, treatment element 18, and/or the encapsulation member 20 to extend away from the handle element 20, and to further protrude a greater distance from the distal end of the elongate body 12. For example, as shown in FIG. 7, the tensioning element 36 may include a spring 38 having first and second ends, with the first end coupled to a portion of the guidewire lumen 16, and the second end coupled to the handle element 20. In a first state, the spring 38 provides a resistive force that biases the guidewire lumen 16 in a direction away from the handle element 20. During use of the medical device 10, the treatment element 18 may be inflated, causing the treatment element 18 to expand and thereby causing the guidewire lumen 16 to retract somewhat in the direction of the handle 20, i.e., the force resulting from the expansion of the treatment element 18 overcomes and/or dominates the force provided by the spring 38. When the treatment element 18 begins to deflate, the bias provided by the spring 38 then shifts the guidewire lumen 16 away from the handle 21, thereby placing tension on the treatment element 18 and the encapsulation member 20. Similar to the operation of the spring 38, additional and/or alternative structures may be employed to provide a biasing force that is ultimately communicated to the treatment element 18.

Figure 8:
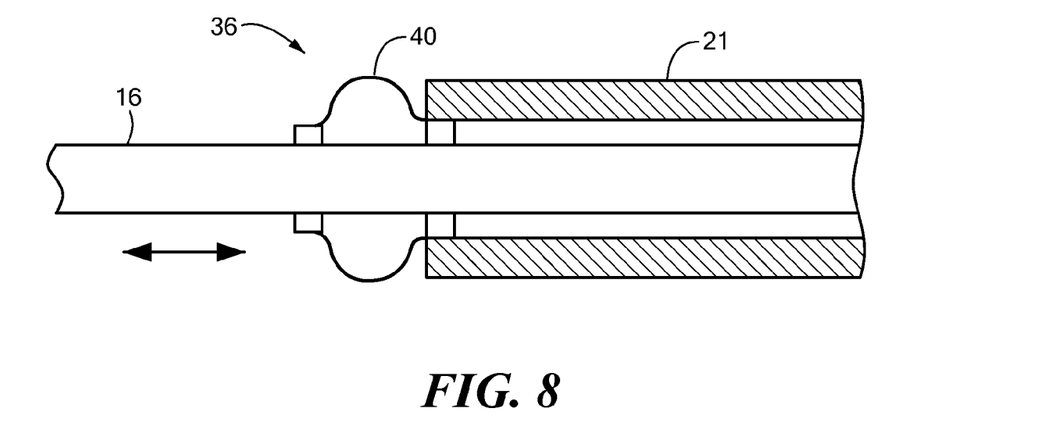
FIG. 8 shows an embodiment of an additional tensioning element in accordance with the present invention.
Figure 9:
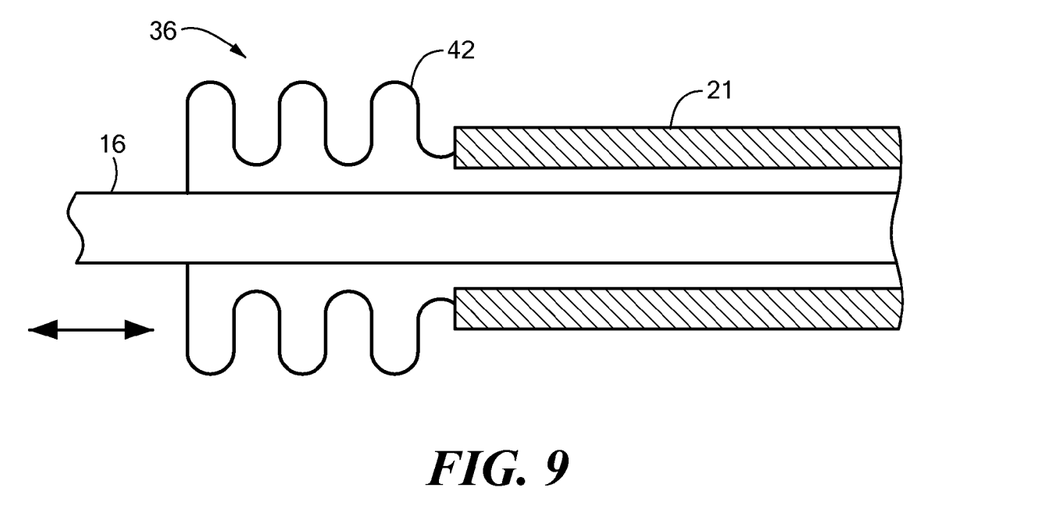
FIG. 9 shows an embodiment of a tensioning element in accordance with the present invention.
Figure 10:
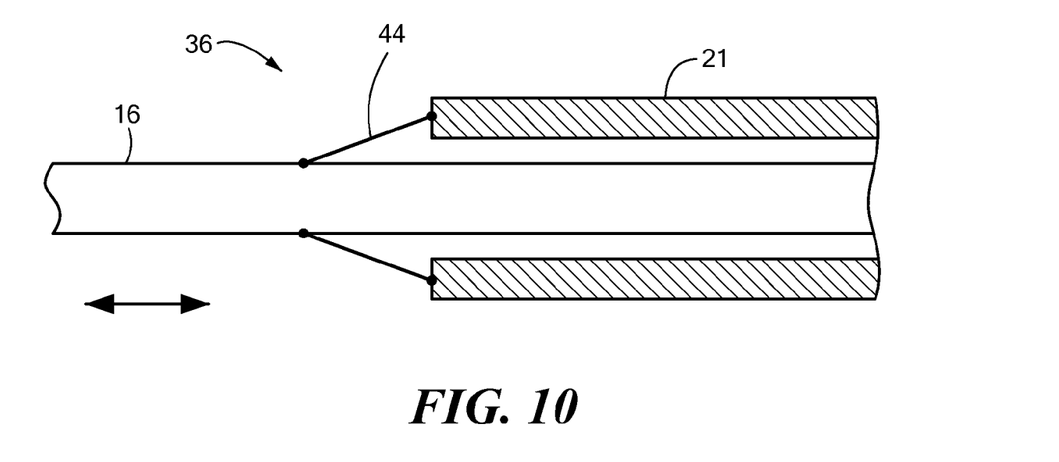
FIG. 10 illustrates an embodiment of another tensioning element in accordance with the present invention.

As shown in FIGS. 8-10, for instance, a compliant balloon 40 could be disposed about the guidewire lumen 16 and/or the handle to provide the desired bias, or a bellow structure 42 could be integrated into the medical device 10. In addition, an elastic member 44 could be coupled to handle and/or guidewire lumen 16 to counter the forces experienced during inflation or extension of the treatment element 18.

Referring again to FIGS. 1 and 2, in addition, the medical device 10 of the present invention may include an actuator element 46 that is movably coupled to the proximal portion of the elongate body 12 and/or the handle 21, and further coupled to the proximal portion of the guidewire lumen 16. Accordingly, manipulating the actuator element 46 in a longitudinal direction may cause the guidewire lumen 16, encapsulation member 20, and/or the treatment element 18 to slide, retract, or otherwise move towards either of the proximal or distal portions of the elongate body 12. As a portion of the treatment element 18 may be coupled to the guidewire lumen 16, manipulation of the actuator element 46 may further cause the treatment element 18 to be tensioned or loosened, depending on the direction of movement of the actuator element 46, and thus, the guidewire lumen 16. Accordingly, the actuator element 46 may be used to provide tension on the treatment element 18 during a particular duration of use of the medical device 10, such as during a deflation sequence, for example. In addition, the actuator element 46 may be used in controlling a particular geometric configuration and/or dimension of the treatment element 18, i.e., the actuator element 46 may exert a tensile force on the encapsulation member 20 or the treatment element 18 to provide for an elongated, cylindrical shape. Subsequently, the actuator element 46 may be retracted to allow the encapsulation member 20 or treatment element 18 to assume a spherical shape having a larger radius than that of the elongated shape experienced under tension.

Figure 11:
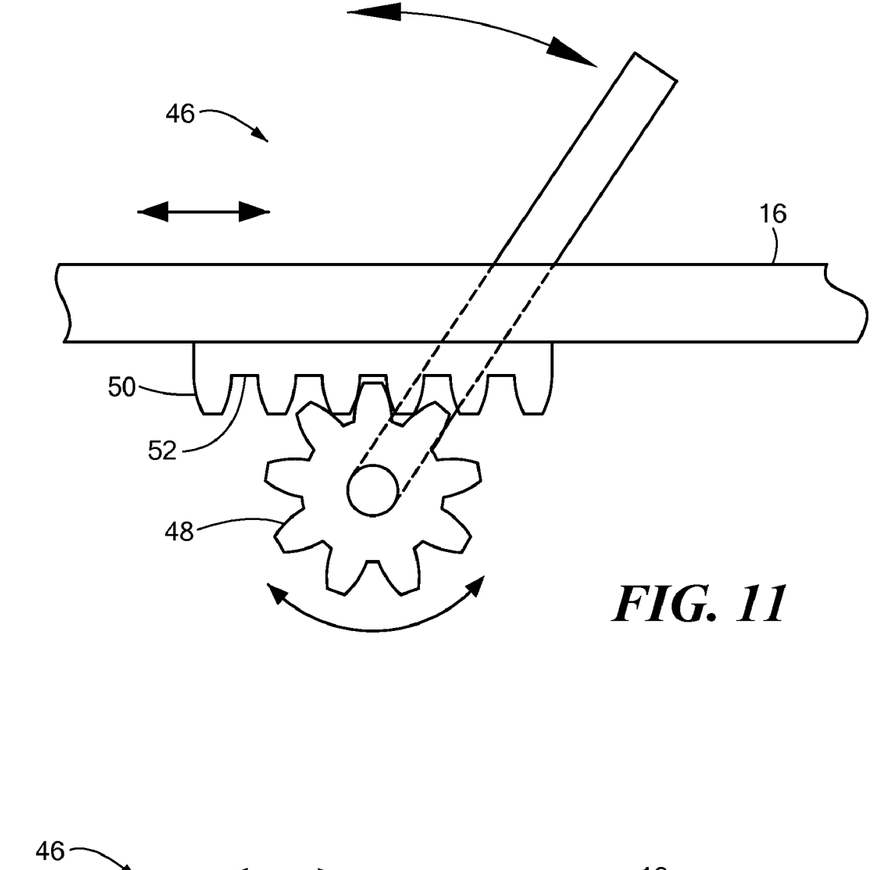
FIG. 11 illustrates an embodiment of an actuator element in accordance with the present invention.
Figure 12:
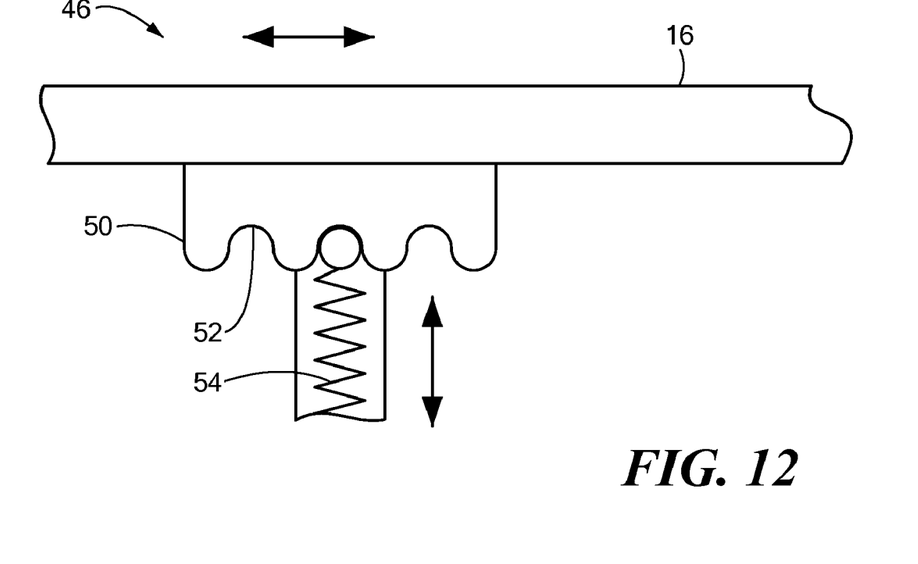
FIG. 12 shows an embodiment of an additional actuator element in accordance with the present invention.
Figure 13:
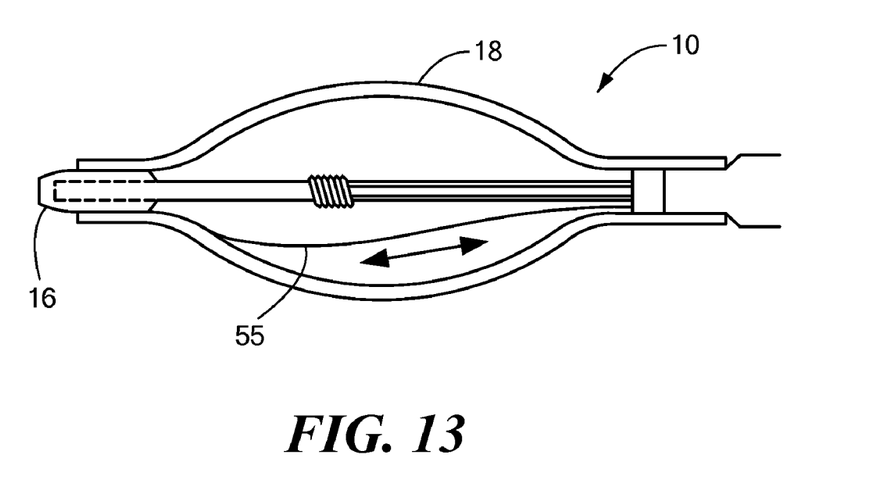
FIG. 13 shows an embodiment of an actuator element in accordance with the present invention.
Figure 14:
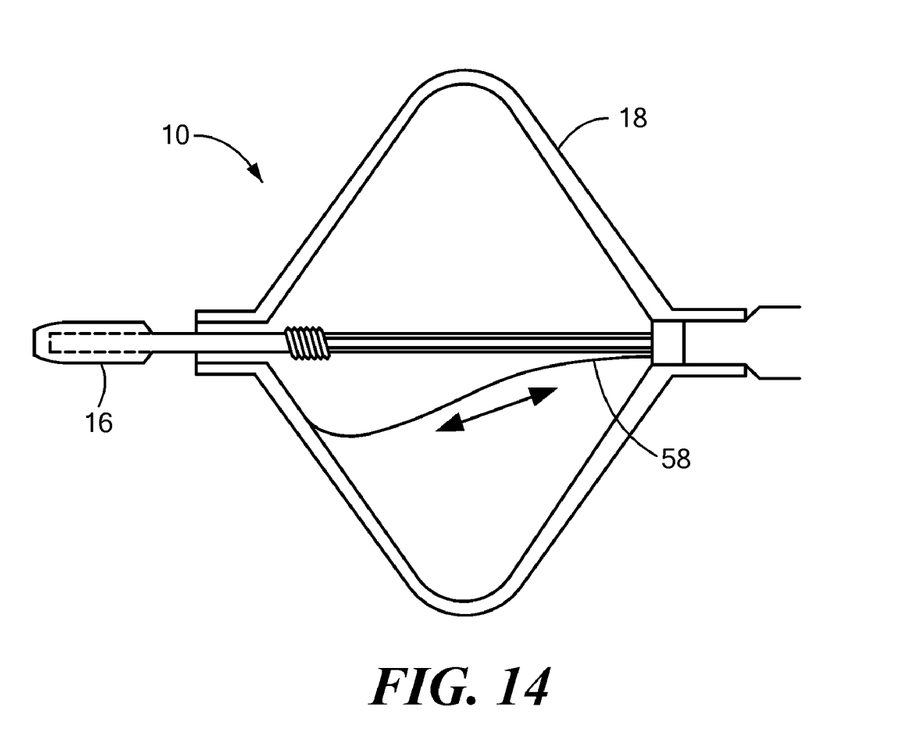
FIG. 14 is an additional illustration of the actuator element of FIG. 13.

The actuator element 46 may include a thumb-slide, a push-button, a rotating lever, or other mechanical structure for providing a movable coupling to the elongate body 12, the handle, the encapsulation member 20 and/or the guidewire lumen 16. Moreover, the actuator element 46 may be movably coupled to the handle such that the actuator element 46 is movable into individual, distinct positions, and is able to be releasably secured in any one of the distinct positions. As shown in FIGS. 11 and 12, for example, the actuator element 46 may include a gear 48 having a plurality of protrusions, and the handle element 20 and/or guidewire lumen 16 may include a track 50 having a plurality of indentations 52. The gear 48 may be rotated to provide for longitudinal advancement or retraction such that the plurality of protrusions sequentially engage the plurality of indentations 52 on the track. Similarly, the actuator element 46 may include a spring-loaded ball 54 which is biased towards engaging the plurality of indentations 52 of the track 50. To move the actuator element 46, the biasing force of the spring may be overcome to allow the actuator element 46, and thus the guidewire lumen, to be advanced or retracted in a controlled manner along the multiple positions provided by the indentations of the track. As shown in FIGS. 13 and 14, a pull wire 55 may be coupled to a portion of the treatment element 18 and or the encapsulation member 20 for tensioning and/or loosening during a procedure. The medical device 10 may further include visible indicia located on the handle element 21 in proximity to each distinct position in which the actuator element 46 may be located, where the indicia may directly correspond to a given dimension and/or shape the treatment element 18 resulting from the particular position of the actuator element 46.

As shown in FIGS. 1 and 2, the medical device 10 of the present invention may further include a size detection element 56 for determining and/or indicating a particular dimension of the treatment element 18 at any given time during a procedure in which the medical device 10 is in use. The size detection element 56 may include a component capable of providing a resistance, impedance, or capacitance measurement that may be correlated to a particular state of the treatment element 18. For example, the size detection element 56 may include a potentiometer coupled to the handle element 21, the guidewire lumen 16 and/or the actuator element 46. When the actuator element 46, and thus the guidewire lumen 16, the treatment element 18 and/or the encapsulation member 20, are in a first position, a resistance, impedance, or capacitance measurement may be indicated by the potentiometer of the size detection element. This measurement may be correlated to a particular dimension, i.e., length, radius, etc., of the treatment element 18 (it is understood that the medical device 10, treatment element 18, and size detection element 56 may need to be initially calibrated or measured in order to determine the relationship between the measurement taken by the size detection element and the corresponding dimension of the treatment element 18). Subsequently, the actuator element 46, guidewire lumen 16, treatment element 18, and/or the encapsulation member 20 may be moved into a second position and/or state. This movement causes a change in the resistive, capacitive, or impedance characteristics of the potentiometer. A corresponding resistance, impedance, or capacitance measurement may again be indicated by the potentiometer of the size detection element 56 to provide information regarding the particular dimensions of the treatment element 18 in the second position. The information regarding the particular dimensions and/or state of the treatment element 18 may be relayed to the control console 34 and used to determine desirable flow rates, temperatures, etc. for appropriate operation of the medical device 10.

An exemplary use of the medical device 10 of the present invention may include making ablative lesions having varying geometric shapes and/or dimensions on a desired tissue region. In such a procedure, the distal portion of the medical device 10 may be positioned in proximity to a tissue region to be treated. The treatment element 18 may be in a first geometric configuration during routing though a portion of the vasculature and positioning in proximity to the region to be treated. For example, the treatment element may be in a relatively narrow, elongated state, such as that shown in FIG. 3. In this first geometric configuration, the granules 19 may be dispersed within the encapsulating member 20 along a length of the extended treatment element 18. The first geometric configuration may be secured at least in part by the biasing forces of a tensioning element (as discussed above) and/or by manipulation of the actuator element 46 and its resulting effect on the guidewire lumen 16, the treatment element 18, and/or the encapsulating member 20. Once the treatment element 18 is in a desired position, it may be selectively transitioned into a second geometric configuration, such as those illustrated in FIGS. 4-6, for example. The particular size and/or dimensions of the treatment element 18 may be monitored through the size detection element 56. The second geometric configuration may be achieved by manipulating the actuator element 46 and its resulting effect on the guidewire lumen 16, the treatment element 18, and/or the encapsulating member 20. For example, the actuation member 46 may be moved to draw a distal portion of the encapsulation member 20 towards the proximal end of the elongate body, thereby moving the plurality of granules 19 in a proximal direction also. The proximal movement of the granules may then cause an expansion of the radius of the treatment element 18, while also reducing its length. In short, movement of the granules 19 and the encapsulation member 20 result in a change in the shape and/or dimensions of the treatment element 18.

The presence of the granules 19 in the treatment element 18 allow the selective change from one shape or geometric configuration to another without the introduction of an expansion fluid or coolant. The granules 19 provide structural reinforcement and "filler" that may prevent the collapse of the treatment element 18 that may otherwise occur under the loads experienced from the surrounding tissue in the absence of an inflation medium or fluid. Furthermore, the structural support of the granules 19 also allows for lower pressures within the treatment element 18 which would otherwise cause the treatment element to collapse. Lower pressures within the treatment element 18 can result in lower ablation temperatures of a circulated coolant, thereby improving the overall thermal efficacy of the medical device 10. The granules can also provide a sufficiently rigid structure to impart a secure and/or forceful contact of the treatment element onto the surrounding tissue through application of a force or torque on the proximal end of the medical device, while also providing a degree of pliability or conformable attribute to deform to an uneven topography of the tissue to be treated.

Once the desired geometric configuration and positioning of the treatment element 18 is achieved, a fluid, such as a cryogenic coolant, may be circulated through the medical device 10 and through the treatment element 18 in order to thermally affect the tissue region and/or to create a tissue lesion having a desired shape. Upon achieving the desired treatment effect, the flow of coolant through the treatment element may be discontinued. The medical device 10 may then be repositioned in proximity to a tissue region where additional thermal treatment may be performed. The treatment element 18 may subsequently be transitioned from the second geometric configuration to a third geometric configuration. The transition may be achieved by imparting a mechanical, thermal, and/or electrical force on the treatment element 18 and/or encapsulation member 20, and may further include manipulation of the actuator element 46. Once the desired geometric configuration has been achieved, the treatment element 18 may once again receive the aforementioned coolant, for example. Accordingly, the third geometric configuration may be used to impart a second tissue lesion and/or thermally affected area having a varied geometric pattern and/or dimension to that of the first tissue lesion.

The ability to selectively change the dimensions of the treatment element 18 allows a single medical device to accommodate anatomical differences experienced from one patient to another (e.g., one patient may require a particular treatment element radius, while a different patient may require an increased treatment element radius), while also providing a single device with the ability to provide multiple ablation treatment patterns (e.g., elongated, annular, etc.) within a single patient. The need for multiple devices having differing, but fixed, shapes or sizes is reduced or eliminated altogether.

Although the exemplary use described above employed three geometric configurations, it is contemplated that a shaping element capable of numerous configurations may be employed and achieved through a combination of mechanical, thermal, and/or electrical forces, as well as through characteristics provided through material selection in the construction of the treatment element 18, the granules 19, and/or the encapsulation member 20. Moreover, while examples and illustrations of particular geometric configurations have been provided, it is understood that virtually any shapes, configurations, and/or dimensions may be included and/or achieved by the medical device of the present invention, including but not limited to those shapes illustrated and described herein. A particular geometric configuration may include circular, conical, concave, convex, rounded, or flattened features and/or combinations thereof. Accordingly, an embodiment of the medical device of the present invention may be able to provide focal lesions, circular lesions, linear lesions, circumferential lesions, and combinations thereof having varying dimensions.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
 a thermal treatment element;
 a plurality of granules disposed within the thermal treatment element; and
 an encapsulation member disposed between the treatment element and plurality of granules and at least partially surrounding the plurality of granules, the encapsulation member being selectively manipulatable to transition the plurality of granules from a first geometric configuration to a second geometric configuration.

2. The medical device according to claim 1, further comprising an actuator element coupled to the encapsulation member for selective adjustment thereof.

3. The medical device according to claim 1, further comprising a tensioning element biasing the plurality of granules towards the first geometric configuration.

4. The medical device according to claim 1, wherein the treatment element is a balloon.

5. The medical device according to claim 1, further comprising a cryogenic fluid source in fluid communication with the thermal treatment element.

6. A cryogenic medical device, comprising:
 a catheter body defining a proximal portion and a distal portion;
 an expandable treatment element on the distal portion of the catheter body;
 a plurality of granules disposed within the expandable treatment element;
 an encapsulation member disposed between the treatment element and plurality of granules and surrounding the plurality of granules, the encapsulating member having a plurality of selectable geometric configurations; and
 an actuator element coupled to the encapsulation member for the selective adjustment thereof.

7. The medical device according to claim 6, further comprising a tensioning element coupled to the encapsulation member, wherein the tensioning element biases the encapsulation member towards a pre-determined geometric configuration.

8. The medical device according to claim 6, further comprising a handle element coupled to the proximal portion of the catheter body.

9. The medical device according to claim 8, wherein the tensioning element and the actuator element are further coupled to the handle element.

10. The medical device according to claim 9, wherein the actuator element is releasably securable in a plurality of discrete positions on the handle element.

11. The medical device according to claim 6, further comprising a size detection element coupled to the treatment element.

12. The medical device according to claim 11, wherein the size detection element includes one of a resistance element, a capacitance element, and an impedance element.

13. A method for thermally affecting a tissue region, comprising:
 positioning a treatment element of a medical device proximate a tissue region, the medical device including an encapsulation member disposed between the treatment element and a plurality of granules and surrounding the plurality of granules the treatment element containing a plurality of granules in a first geometric configuration;
 controllably and selectively transitioning the encapsulation member to cause the plurality of granules to transition from the first geometric configuration to a second geometric configuration; and
 delivering a cryogenic coolant into the treatment element, thereby thermally affecting the tissue region.

14. The method according to claim 13, wherein controllably transitioning the plurality of granules from the first geometric configuration to a second geometric configuration includes manipulating an actuator element coupled to the encapsulation member.

15. The method according to claim 13, further comprising terminating the cryogenic coolant delivery.

16. The method according to claim 15, further comprising controllably transitioning the plurality of granules from the second geometric configuration to the first geometric configuration.

17. The method according to claim 15, further comprising controllably transitioning the plurality of granules from the second geometric configuration to a third geometric configuration.

18. The method according to claim 13, wherein the tissue region includes cardiac tissue.

* * * * *